United States Patent [19]

Oka et al.

[11] Patent Number: 5,886,122

[45] Date of Patent: Mar. 23, 1999

[54] PROCESS FOR PREPARING SOLVENT-TYPE ACRYLIC PRESSURE-SENSITIVE ADHESIVES AND MEDICAL PRESSURE-SENSITIVE ADHESIVE

[75] Inventors: Takayuki Oka; Kenji Tsubota; Takashi Shinjo, all of Osaka; Takeshi Nakachi; Mitsue Matsumoto, both of Shinnanyo; Motoi Nagano, Osaka, all of Japan

[73] Assignee: Sekisui Kagaku Kogyo Kabushiki Kaisha, Osaka, Japan

[21] Appl. No.: 913,475

[22] PCT Filed: Mar. 26, 1996

[86] PCT No.: PCT/JP96/00790

§ 371 Date: Sep. 15, 1997

§ 102(e) Date: Sep. 15, 1997

[87] PCT Pub. No.: WO96/30416

PCT Pub. Date: Oct. 3, 1996

[30] Foreign Application Priority Data

| Mar. 31, 1995 | [JP] | Japan | 7-075973 |
| Mar. 31, 1995 | [JP] | Japan | 7-075975 |
| Mar. 31, 1995 | [JP] | Japan | 7-075983 |
| Sep. 21, 1995 | [JP] | Japan | 7-243078 |
| Oct. 31, 1995 | [JP] | Japan | 7-283240 |

[51] Int. Cl.$^6$ .................................. C08F 20/10
[52] U.S. Cl. .................. 526/328; 526/258; 526/317.1
[58] Field of Search .................. 526/328, 258, 526/318.1

[56] References Cited

U.S. PATENT DOCUMENTS

| 4,912,184 | 3/1990 | Akasaki et al. ............. 526/328 |
| 5,028,674 | 7/1991 | Hatch et al. ............. 526/328 |
| 5,153,286 | 10/1992 | Mayo et al. ............. 526/328 |
| 5,283,092 | 2/1994 | Everaerts et al. ............. 526/328 |
| 5,322,912 | 6/1994 | Georges et al. ............. 526/328 |
| 5,328,947 | 7/1994 | Taguchi et al. ............. 526/328 |
| 5,688,883 | 11/1997 | Klee et al. ............. 526/328 |

FOREIGN PATENT DOCUMENTS

| 0463384 | 1/1971 | Japan ............. 526/328 |
| 0378403 | 7/1973 | U.S.S.R. ............. 526/328 |

*Primary Examiner*—Bernard Lipman
*Assistant Examiner*—N. Sarofim
*Attorney, Agent, or Firm*—Armstrong, Westerman, Hattori, McLeland & Naughton

[57] ABSTRACT

The object is directed toward obtaining a process for preparing a solvent-type acrylic pressure-sensitive adhesive which is able to increase a conversion at polymerization in the preparation of the solvent-type acrylic pressure-sensitive adhesive to thereby solve the problems of odors associated with residual monomers and of attachment of gels on reactor walls, and further to provide improved productivity and workability.

In the preparation of the solvent-type acrylic pressure-sensitive adhesives, a monomer composition containing alkyl (meth)acrylate ester as its main component is subjected to solution polymerization under a closed condition at least in a latter stage of the polymerization reaction. In the polymerization, the solution to be polymerized is maintained at temperatures not lower than a boiling point thereof under normal pressures or at 50°–120° C.

19 Claims, No Drawings

PROCESS FOR PREPARING SOLVENT-TYPE ACRYLIC PRESSURE-SENSITIVE ADHESIVES AND MEDICAL PRESSURE-SENSITIVE ADHESIVE

FIELD OF THE INVENTION

The present invention relates to a method for preparing solvent-type acrylic pressure-sensitive adhesives and a medical pressure-sensitive adhesive utilizing the pressure-sensitive adhesives. More particularly, this invention relates to a method for preparing solvent-type acrylic pressure-sensitive adhesives for use in pressure-sensitive adhesive-coated products in such forms as tapes and labels, and in medical adhesive materials known as plasters and poultices; and to a medical pressure-sensitive adhesive utilizing the above solvent-type acrylic pressure-sensitive adhesives for exhibiting a marked reduction in residual monomers content which may otherwise cause irritation to human body.

DESCRIPTION OF THE PRIOR ART

Conventionally, pressure-sensitive adhesive-coated products, such as pressure-sensitive adhesive tapes and sheets, have been widely used in such applications as building materials, household electrical appliances, automotive cushioning materials, gap-filling tapes and the like. Exemplary forms of such pressure-sensitive adhesive tapes and sheets include double-coated tapes having pressure-sensitive adhesive layers provided on opposite surfaces of a substrate, foam tapes having pressure-sensitive adhesive layers provided on at least one surface of a foam substrate, commonly-used pressure-sensitive adhesive tapes having a pressure-sensitive adhesive layer provided on a single surface of a suitable substrate and the like.

In a medical field, medical adhesive materials have been widely employed which typically define a drug-containing pressure-sensitive adhesive layer on a substrate. Another type of medical adhesive materials incorporates a drug-free pressure-sensitive adhesive layer provided on at least one surface of a flexible sheet or tape substrate, such as for use as adhesive bandages and the like.

Most representative of pressure-sensitive adhesives for use in varieties of pressure-sensitive adhesive-coated products and medical adhesive materials as mentioned above are solvent-type pressure-sensitive adhesives comprised primarily of acrylic copolymers. This is because the solvent-type acrylic pressure-sensitive adhesives exhibit excellent performance characteristics including weatherability, durability, heat resistance, freeze resistance and water resistance.

The solvent-type acrylic pressure-sensitive adhesives have also come into widespread use as pressure-sensitive adhesives for constituting a pressure-sensitive adhesive layer in medical adhesive materials, since their physical properties, including a tack strength, can be readily controlled by combining various types of acrylic monomers.

The above-described, acrylic pressure-sensitive adhesives are obtainable generally by polymerizing a monomer composition containing as its main component alkyl (meth) acrylate ester through solution or emulsion polymerization, introducing additives and others to the resulting polymer solution, and thereafter removing a solvent by drying. When manufacturing medical adhesive materials, purposed drugs are added to the above-mentioned polymer solution prior to removal of the solvent by drying.

In medical practices, nitroglycerin-containing medical adhesive materials of endermic absorption type are employed as remedies or prophylactics for heart disease such as angina pectoris, myocardial infarction or heart failure. For example, Japanese Patent Laying-open No. Sho 63-246325 discloses nitroglycerin-containing adhesive materials which utilize particular alkyl (meth)acrylate ester copolymers.

It is known that endermic preparations which utilize a medical pressure-sensitive adhesive comprising a copolymer of alkyl (meth)acrylate ester and vinyl pyrrolidone, among the above-described acrylic pressure-sensitive adhesives, are capable of exhibiting effects of active ingredients in a short period after application as well as their effectiveness for a prolonged period of time (Japanese Patent publication No. Hei 3-70685).

BACKGROUND OF THE INVENTION

The widespread uses of the above-described, typical pressure-sensitive adhesive-coated products have accompanied increased odor problems associated with residual acrylic monomers in the solvent-type acrylic pressure-sensitive adhesives. It is accordingly desired to provide pressure-sensitive adhesive-coated products which release less odors as a result of reduced residual acrylic monomers. Furthermore, a strong demand has arisen for the reduced odor of residual acrylic monomers which results in improved working atmospheres under which pressure-sensitive adhesives are manufactured.

In the manufacture of the solvent-type acrylic pressure-sensitive adhesives, various methods have been attempted to achieve odor reduction as mentioned above, examples of which include a method which attempts to enhance a conversion by increasing catalysts in amount, a method in which a polymerization reaction period is prolonged, a method which attempts to add an increased amount of initiator in a latter stage of the polymerization reaction, and a method which involves the repeated addition of an initiator during the polymerization reaction.

However, those methods involving either adding the increased amount of initiator in the latter stage of the polymerization reaction or repeatedly adding the initiator during the polymerization reaction sometimes caused significant change in pressure-sensitive adhesive properties thereof with time, while effective in lowering the residual monomers content. In particular, among the pressure-sensitive adhesive properties, a holding power was observed to sometimes change largely with time.

Also, in Japanese Patent Laying-open No. Sho 63-175086, a method is disclosed which adds scavenger monomers after substantial completion of polymerization to reduce residual monomers. This method however resulted in substantially inadequate reaction of the scavenger monomers to leave them as residues so that it failed to reduce odors to a satisfactory extent.

While the reduced odor is pursued, an extremely reduced level of residual monomer concentration is highly sought for the medical adhesive materials utilizing the solvent-type acrylic pressure-sensitive adhesives, from additional considerations of preventing them from causing irritation, rash, itch and erythema to human body. To this end, a proposal has been made to provide a medical pressure-sensitive adhesive which, prior to introducing drugs thereto, contains therein residual monomers in an amount not to exceed 0.2 weight % of a total amount of the adhesive, on a solids content basis (Japanese Patent Laying-open No. Hei 5-131022).

A reduced degree of change in pressure-sensitive adhesion with time is highly sought for the pressure-sensitive adhesive-coated products and medical adhesive materials. In particular, for the medical adhesive materials which are applied to human body in use, such a change in pressure-sensitive adhesion with time significantly affects comfort to human body during use thereof. For example, any increase in pressure-sensitive adhesion with time may cause damages to human skin when separating the medical adhesive material therefrom. In another event where the pressure-sensitive adhesive layer increases its stiffness with time, a stress thus applied to human skin during use may cause an increased degree of irritation to human skin.

On the other hand, any reduction in pressure-sensitive adhesion with time may cause the medical adhesive material to be separated from human skin or to be partially lifted during use thereof.

In recent years, it has been highly sought that the preparations of endermic absorption type give reduced irritation to human skin during use thereof. One known method to reduce irritation to skin involves adding to the pressure-sensitive adhesive a liquid component which is compatible therewith. However, this method reduces cohesion of the pressure-sensitive adhesive to cause problems of staying or legginess thereof upon release from human skin, while effective in reducing irritation due to a plasticizing action of the liquid component.

In Japanese Patent Laying-open No. Hei 3-223212, a method is disclosed for preventing reduction in cohesion of the pressure-sensitive adhesive to relax or disperse a stress applied to human skin upon release of a medical adhesive material therefrom and thereby optimize a balance between adhesion and irritation to human skin, by introducing a liquid component into a pressure-sensitive adhesive which is subsequently coated and followed by a crosslinking treatment to form oily gels. There still remains a problem that the residue of unreacted initiators in a pressure-sensitive adhesive layer causes irritation to human skin.

Also, Japanese Patent Publication No. Hei 2-28978 discloses a method wherein a pressure-sensitive adhesive is slightly pre-crosslinked with polyfunctional monomers.

In the above case where a polymerization reaction period is prolonged to reduce residual monomers to a possible extent, a lowered productivity results. In addition, the production of gels insoluble in a solvent is encouraged to possibly allow the gels to attach to reactor walls. As a result, another problem arises which necessitates troubled operations such as for cleaning the reactor.

In particular, those methods, as described above, which either pre-crosslink the pressure-sensitive adhesive with polyfunctional monomers or effect polymerization utilizing a highly concentrated monomer solution for increasing a molecular weight of a resulting copolymer, accompany attachment of a large amount of gels onto the reactor walls. This consequently renders the operations, such as for cleaning the reactor, more troublesome to result in substantially lowered productivity and workability in the manufacture of the pressure-sensitive adhesives.

Furthermore, the formation of the above-mentioned gels in a pressure-sensitive adhesive solution causes reduced coatability of the pressure-sensitive adhesives and difficulty in obtaining preferred quality of endermic preparations.

SUMMARY OF THE INVENTION

It is an object of the invention to provide a process for preparing solvent-type acrylic pressure-sensitive adhesives whereby the above-described problems encountered with the conventional solvent-type acrylic pressure-sensitive adhesives can be solved and a conversion in solution polymerization can be enhanced to result in reduced odors of the pressure-sensitive adhesives commensurate with reduced amounts of residual monomers and improved productivity and workability.

It is also an object of the present invention to provide a highly productive and workable process for preparing solvent-type acrylic pressure-sensitive adhesives which, when employed as a medical pressure-sensitive adhesive, exhibit less change in its pressure-sensitive adhesion with time.

It is further an object of the invention to provide a medical pressure-sensitive adhesive which exhibits reduced odors associated with residual monomers and less change with time in pressure-sensitive adhesion, and which can be prepared with high productivity.

In accordance with a broad aspect of the invention, for the purposes of solving the problems as described above, a process for preparing solvent-type acrylic pressure-sensitive adhesives is provided which is characterized by subjecting to solution polymerization a monomer composition containing as its main component alkyl (meth)acrylate ester under a closed condition at least in a latter stage of the polymerization reaction in the presence of a radical initiator such that the residual initiator content in the pressure-sensitive adhesive is not higher than 0.05 weight % of a total weight on a solids content basis.

In significance, the process for preparing a solvent-type acrylic pressure-sensitive adhesive in accordance with the present invention is characterized in that the monomer composition containing as its main component alkyl (meth) acrylate ester is subjected to solution polymerization under a closed condition at least in the latter stage of the polymerization reaction.

Examples of solvents useful for the solution polymerization include ester solvents such as ethyl acetate, propyl acetate and butyl acetate; ketone solvents such as methyl ethyl ketone and cyclohexanone; aromatic solvents such as benzene and toluene; and Cellosolve solvents such as methyl Cellosolve and ethyl Cellosolve. The solvent may be employed alone or in combination with one or more other solvents.

In accordance with the present invention, the above-stated monomer composition containing as its main component alkyl (meth)acrylate ester is subjected to solution polymerization under a closed condition at least in the latter stage of the polymerization reaction. Such a solution polymerization under the closed condition may be effected by utilizing a polymerization reactor capable of defining a closed system. For example, a polymerization reactor is charged with a nitrogen gas to discharge air remaining in the reactor, followed by exclusion of the nitrogen gas using a vacuum pump to maintain an interior of the reactor under vacuum pressure (10–200 mmHg) prior to effecting the solution polymerization.

Any reactor which has a pressure-resistant structure can be employed as the above-described polymerization reactor. Various shapes of reactors can be employed, examples of which include tank-, column-, and vessel-shaped reactors.

The solution polymerization needs to be effected under a closed condition at least in the latter stage of the polymerization reaction. Accordingly, the solution polymerization can be effected under the closed condition over entire steps of the polymerization reaction. Alternatively, such a closed condition can be applied at a stage subsequent to a midpoint of the polymerization reaction.

The term "latter stage of the polymerization reaction", as used in the above expression "under a closed condition at least in the latter stage of the polymerization reaction", means a state in which a conversion has reached 95% or greater.

In accordance with the present process for preparing solvent-type acrylic pressure-sensitive adhesives, the monomer composition containing as its main component alkyl (meth)acrylate ester, as hereinafter described, is supplied into the above-described reactor. In such an event, an undivided whole of the required amount of each monomer component which constitutes the monomer composition may be supplied at one time. Alternatively, suitably divided fractions thereof may be supplied at intervals. If necessary, a polymerization initiator as hereinafter described may be supplied to allow the polymerization reaction to proceed. Likewise, an undivided whole or divided fractions of a predetermined amount of the initiator may be supplied to the reactor at one time or at intervals.

In accordance with the present invention, the polymerization reaction is effected under a closed condition, as described above. This allows a reaction temperature to be set to not lower than a boiling point of a solvent used under normal pressures. In such an event that the reaction temperature is set to not lower than the boiling point of the solvent under normal pressures, the equilibrium relationship of liquid and vapor phase portions is established within the reactor. On the other hand, in the case of setting to not higher than the boiling point, a portion of the solvent is in a vapor state.

While a pressure developed within the reactor corresponds to a vapor pressure of the solvent at a predetermined temperature, the pressure increase is too slight to create any substantial problems since gaseous components are removed in an early stage.

As described above, effecting the polymerization at a temperature not lower than the boiling point of the solution to be polymerized under normal pressures enables an enhanced conversion, as a result of which the residual monomers content can be reduced without using a prolonged reaction period.

In accordance with a particular aspect of the present invention, the solution polymerization is effected under a closed condition at a reaction temperature in the range of 50°–120° C. Effecting the polymerization at an excessively low reaction temperature possibly results in a reduced reactivity, which necessitates a prolonged reaction period leading to a low productivity. On the other hand, a higher reaction temperature acts to increase an initial reactivity to possibly result in difficulty in controlling the polymerization reaction. Thus, the reaction temperature is preferably in the range of 50°–120° C., as stated above, more preferably in the range of 60°–100° C. When effecting the reaction, the reaction temperature may be maintained constant or varied within the above-specified preferred temperature range at suitable time intervals.

THE MONOMER COMPOSITION

As described above, the present invention utilizes the monomer composition containing as its main component alkyl (meth)acrylate ester. The type of alkyl (meth)acrylate ester is not particularly specified. Examples of alkyl residues contained in alkyl (meth)acrylate ester include methyl, ethyl, propyl, isopropyl, n-butyl, isobutyl, n-hexyl, isohexyl, 2-ethylhexyl, n-octyl, isooctyl, nonyl, decyl, lauryl, and stearyl groups. One or more of these groups may be used.

Any alkyl (meth)acrylate ester which contains one or more of the above-listed alkyl residues can be employed in the present invention. Those alkyl (meth)acrylate esters can be employed which contain an alkyl group having 1–18 carbon atoms. Illustrative of such alkyl (meth)acrylate esters include methyl (meth)acrylate, ethyl (meth)acrylate, propyl (meth)acrylate, isopropyl (meth)acrylate, n-butyl (meth)acrylate, isobutyl (meth)acrylate, n-hexyl (meth)acrylate, isohexyl (meth)acrylate, n-octyl (meth)acrylate, isobutyl (meth)acrylate, 2-ethylhexyl (meth)acrylate, nonyl (meth)acrylate, decyl (meth)acrylate, lauryl (meth)acrylate, stearyl (meth)acrylate and any combination of one or more of the above.

Those preferred for use as the above-mentioned alkyl (meth)acrylate ester are alkyl (meth)acrylate esters containing an alkyl group having 2–12 carbon atoms, examples of which include ethyl (meth)acrylate, butyl (meth)acrylate, 2-ethylhexyl (meth)acrylate and lauryl (meth)acrylate. In the case where the number of carbon atoms contained in the alkyl group is equal to 1 or higher than 12, the use of alkyl (meth)acrylate esters containing such an alkyl group possibly leads to inadequacy in pressure-sensitive adhesion of the solvent-type acrylic pressure-sensitive adhesives prepared.

As used herein, the term (meth)acrylate is intended to include acrylate and methacrylate.

The monomer composition in accordance with the present invention may further incorporate a monomer copolymerizable with the alkyl (meth)acrylate ester. Such a monomer to be copolymered with the alkyl (meth)acrylate ester may be suitably selected from monomers which have been conventionally employed for copolymerization with alkyl (meth)acrylate esters in the preparation of acrylic pressure-sensitive adhesives, depending upon the pursued pressure-sensitive adhesive properties. Illustrative of the monomers to be copolymerized with the alkyl (meth)acrylate ester are vinyl acetate, vinyl pyrrolidone, diacetone acrylamide, acrylonitrile, dimethyl acrylamide, ethylene glycol mono (meth)acrylate ester, and styrene. These monomers can be suitably employed within a range which will not otherwise adversely affect pressure-sensitive adhesion and cohesion of the resulting pressure-sensitive adhesives. A maximum use amount of these monomers is typically 40 mole % of a total mole of the monomer composition.

In accordance with a particular aspect of the present invention, a monomer composition includes alkyl (meth)acrylate ester containing an alkyl group having 2–12 carbon atoms, and a vinyl monomer(s) copolymerizable with alkyl (meth)acrylate ester. Examples of vinyl monomers include, but are not limited to, hydroxyl group-containing monomers such as 2-hydroxyethyl (meth)acrylate, and 2-hydroxypropyl (meth)acrylate; carboxyl group-containing monomers such as (meth)acrylic acid, maleic acid, itaconic acid, and crotonic acid; and other monomers including methyl (meth)acrylate, vinyl acetate, styrene, fluoroacrylate, isononyl (meth)acrylate, (meth)acrylamide, acrylonitrile, and N-vinyl pyrrolidone. Here, the use of the monomer composition comprising alkyl (meth)acrylate ester containing an alkyl group having 2–12 carbon atoms and the vinyl monomer(s) as described above allows adjustment of physical properties such as pressure-sensitive adhesion as well as impartment of properties such as heat-resistance.

In accordance with another particular aspect of the present invention, a monomer composition containing as its main component alkyl (meth)acrylate ester incorporating an alkyl group having 6 or more carbon atoms is employed wherein the alkyl (meth)acrylate ester includes 40 weight % to 90 weight % of 2-ethylhexyl (meth)acrylate. In this instance, if the content of 2-ethylhexyl (meth)acrylate becomes larger, in an exemplary case where a medical adhesive material is prepared utilizing the resulting pressure-sensitive adhesives, it becomes more possible that a pressure-sensitive adhesive layer thereof becomes stiffened and pressure-sensitive adhesion of the layer is reduced to allow the medical adhesive material to be easily separated. On the other hand, in the event that the content of 2-ethylhexyl (meth)acrylate is excessively small, the addition of highly concentrated drugs, such as nitroglycerin, to the monomer composition possibly causes reduced cohesion of the resulting pressure-sensitive adhesives so that the pressure-sensitive layer becomes softer to allow the adhesives to remain upon removal of the medical adhesive material. Thus, the monomer composition is specified as containing 2-ethylhexyl (meth)acrylate preferably in the range of 40–90 weight %, more preferably in the range of 60–80 weight %.

In the case where the number of carbon atoms contained in the alkyl (meth)acrylate ester is small, a saturated solubility therein of drugs such as nitroglycerin is increased to result in enhanced affinity of the resulting copolymer for the drugs. This causes reduction of the drug proportion present in an adhesive layer portion facing toward human skin to result in reduced endermic absorption. Thus, the alkyl (meth)acrylate ester which carries an alkyl group having 6 or more carbon atoms is preferably employed, as described above.

Examples of the alkyl (meth)acrylate esters carrying an alkyl group having 6 or more carbon atoms include n-hexyl (meth)acrylate, isohexyl (meth)acrylate, heptyl (meth)acrylate, n-octyl (meth)acrylate, isobutyl (meth)acrylate, 2-ethylhexyl (meth)acrylate, nonyl (meth)acrylate, decyl (meth)acrylate, dodecyl (meth)acrylate, lauryl (meth)acrylate, and stearyl (meth)acrylate.

In addition to including the above-mentioned 2-ethylhexyl (meth)acrylate, the monomer composition further includes other monomer(s) selected from one or more alkyl (meth)acrylate esters which preferably allow the resulting copolymer to exhibit a ball tack value not exceeding 2.

In accordance with another particular aspect of the present invention, the monomer composition includes 40–99 mole %, preferably 50–97 mole % of alkyl (meth)acrylate ester, and 1–60 mole %, preferably 3–50 mole % of vinyl pyrrolidone. In such a formulation, a suitable type of alkyl (meth)acrylate esters may be selectively employed depending upon its ratio to vinyl pyrrolidone in the resulting copolymer and the pursued properties.

The inclusion of alkyl (meth)acrylate ester is here specified as being in the range of 40–99 mole % due to the following reasons. A lower inclusion of alkyl (meth)acrylate ester possibly causes reduced pressure-sensitive adhesion of the resulting pressure-sensitive adhesives whereas a higher inclusion thereof possibly causes reduced initial drug release of a medical adhesive material prepared from the resulting pressure-sensitive adhesives.

In accordance with still another aspect of the present invention, the monomer composition includes alkyl (meth)acrylate ester, and a polyfunctional monomer which contains 2 or more polymerizable double bonds per molecule, wherein the inclusion of the polyfunctional monomer is 0.001–0.1 moles per 100 moles of alkyl (meth)acrylate ester. In this instance, the alkyl (meth)acrylate ester employed may be selected from alkyl (meth)acrylate esters which carry an alkyl group having 1–18 carbon atoms, as described above.

Examples of the polyfunctional monomers include divinyl benzene, methylene bisacrylamide, ethylene glycol di(meth)acrylate ester, propylene glycol di(meth)acrylate ester, butylene glycol di(meth)acrylate ester, hexylene glycol di(meth)acrylate ester, 1,6-hexanediol di(meth)acrylate ester, polyethylene glycol di(meth)acrylate ester, polypropylene glycol di(meth)acrylate ester, and trimethylolpropane tri(meth)acrylate ester.

An unsatisfactory cohesive effect may result if the content of the polyfunctional monomer is low. A higher content thereof possibly results in difficulty in adjusting a degree of polymerization during reaction, which facilitates gelling of a reaction solution, or makes it difficult to keep a copolymer solution in its stable state for a prolonged period, even though it is possible to obtain the copolymer solution without gelling thereof. Accordingly, the polyfunctional monomer is incorporated in the range of 0.001–0.1 moles, preferably in the range of 0.003–0.07 moles per 100 moles of the alkyl (meth)acrylate ester.

The addition of the polyfunctional monomer, as described above, allows the polymer to be partially crosslinked to be present in a "slightly crosslinked" state, which enables production of a highly polymerized copolymer. This slight crosslink imparts appropriate cohesion to resulting pressure-sensitive adhesives and acts to prevent them from remaining upon release thereof. Also, a pressure-sensitive adhesive solution obtained exhibits an increased degree of stability.

In accordance with still another particular aspect of the present invention, the monomer composition includes 1–10 weight % of monomer(s) which has at least one reactive functional group selected from the group consisting of carboxyl, hydoxyl, amide, epoxy and amino groups. In this instance, the alkyl (meth)acrylate ester as employed may be selected from alkyl (meth)acrylate esters which carry an alkyl group having 1–18 carbon atoms, as described above. The type of such alkyl (meth)acrylate esters may be suitably selected depending upon a desired ratio thereof to a monomer(s) having the reactive functional group, as described below, in the resulting copolymer, as well as the pursued properties.

Examples of the monomers having a carboxyl group include (meth)acrylic acid, crotonic acid, itaconic acid, fumaric acid, and maleic acid.

Examples of the monomers having a hydroxyl group include hydroxyethyl (meth)acrylate, hydroxypropyl (meth)acrylate, mono(hydoxyethyl) maleate, and propylene glycol mono(meth)acrylate.

Illustrative of the monomer having an amide group is (meth)acrylamide.

Illustrative of the monomer having an epoxy group is glycidyl (meth)acrylate.

Examples of the monomers having an amino group include dimethylaminoethyl (meth)acrylate and t-butylaminoethyl (meth)acrylate.

A lower content of the monomer having the reactive functional group, as listed above, results in a reduced crosslinking effect thereof, if crosslinking is performed. A higher content thereof results in reduced pressure-sensitive adhesion of a copolymer obtained, and in poor applicability thereof to human skin. Accordingly, the monomer having the reactive functional group is incorporated in the range of 1–10 weight %, preferably in the range of 2–8 weight % of a total weight of the monomer composition.

More preferably employed as the monomer having the reactive functional group is (meth)acrylic acid. The monomer composition contains preferably 1–10 weight %, more preferably 2–8 weight % of (meth)acrylic acid. This is because if a content of (meth)acrylic acid becomes higher, when a formulation is made by adding a crosslinking agent to a resulting pressure-sensitive adhesive, a more stiffened pressure-sensitive adhesive layer possibly results which has reduced pressure-sensitive adhesion to allow easy separation thereof, and because a lower content of (meth)acrylic acid possibly results in reduced crosslinking effect.

In accordance with still another particular aspect of the present invention, a solvent-type acrylic pressure-sensitive adhesive includes as its main component an acrylic copolymer having a number average molecular weight ranging from 10,000 to 500,000. The acrylic copolymer includes an alkyl (meth)acrylate ester carrying an alkyl group having 2–12 carbon atoms, and a vinyl monomer copolymerizable with the alkyl (meth)acrylate ester. If the number average molecular weight of the acrylic copolymer is less than 10,000, reduction in heat resistance of a resulting pressure-sensitive adhesive results. If it exceeds 500,000, excessive increase in viscosity of a resulting pressure-sensitive adhesive results. Preferably, the acrylic copolymer has a number average molecular weight ranging from 100,000 to 500,000. In this case, a monomer composition for constituting the acrylic copolymer preferably includes 0.01–10 weight % of hydroxyl- and carboxyl-containing monomers. More preferably, the monomer composition includes 0.01–3 weight % of hydroxyl-containing monomer and 1–10 weight % of carboxyl-containing monomer. Inclusion of hydroxyl- and carboxyl-containing monomers in excessively higher proportions causes reduced pressure-sensitive adhesion of a resulting solvent-type acrylic pressure-sensitive adhesive. Inclusion thereof in excessively lower proportions causes decreased elastic modulus of a resulting solvent-type acrylic pressure-sensitive adhesive at elevated temperatures to result in its reduced peel strength under constant load.

In the process for preparing a solvent-type acrylic pressure-sensitive adhesive in accordance with the present invention, the above-described polymerization reaction may be carried out by further adding to the above-mentioned monomers and solvent suitable additives which are commonly used for polymerization reactions, e.g. other monomers or below-described polymerization initiators as required.

POLYMERIZATION INITIATOR

Conventional, thermally-activated radical initiators are useful as the polymerization initiator optionally employed for the present invention, examples of which include organic peroxides such as peroxycarbonates, ketone peroxides, peroxyketals, hydroperoxides, dialkyl peroxides, diacyl peroxides, and peroxyesters (e.g. lauroyl peroxide, and benzoyl peroxide); and azo compounds such as 2,2'-azobisisobutyronitrile, 2,2'-azobis(2-methylbutyro-nitrile), 2,2'-azobis(2,4-dimethylvaleronitrile), and 2,2'-azobis (dimethyl isobutyrate). The initiator for use may be suitably selected from these polymerization initiators, depending upon polymerization temperatures as used. Also, these polymerization initiators can be used alone or in combination.

The amount of the polymerization initiator used is preferably in the range of 0.0001–5 weight parts per 100 weight parts of the monomers which constitute the acrylic copolymer. However, in order to reduce the amount of residual monomers, it generally needs to be not lower than 0.1 weight %.

THE RESIDUAL INITIATOR CONTENT

In accordance with a particular aspect of the present invention, a solution polymerization is carried out such that a residual initiator content in the above-stated acrylic pressure-sensitive adhesive is not higher than 0.05 weight % of a total amount, based on a solids content basis. As such, the residual initiator content of not higher than 0.05 weight % of a total amount, on a solids content basis, is effective in preventing undesirable change in adhesive properties of the pressure-sensitive adhesives with time.

The residual initiator present after the pressure-sensitive adhesive is prepared decomposes with time to generate radicals. This is considered to cause the acrylic pressure-sensitive adhesive to undergo a crosslinking reaction through hydrogen abstraction, or to cause a reaction of the radicals of adding to active groups present in drugs or additives contained therein. It is accordingly desired that the residual initiator content is as low as possible. The inventors of the present application have discovered that any undesirable change of the adhesive properties with time can be effectively prohibited by allowing the residual initiator content not to exceed 0.05 weight % of a total weight of the pressure-sensitive adhesive, on a solids content basis.

More preferably, the residual initiator content may be controlled within 0.01 weight %, which range is more effective in preventing undesirable change of the pressure-sensitive adhesive in adhesive properties with time. If the residual initiator content exceeds 0.05 weight %, on a solids content basis, a significant change with time in adhesive properties possibly results.

An applicable method for reducing the residual initiator content in the pressure-sensitive adhesives is not particularly limited. One exemplary method involves elevating a temperature in the latter stage of the polymerization reaction for maintaining a reaction solution at the elevated temperature for a time period not shorter than required. Considering a time period required for the polymerization, increasing a temperature in the latter stage of the polymerization is a preferred method to successfully reduce the residual initiator content in a shorter period of time. To illustrate this instance more specifically, a method can be adopted in which the reaction solution is refluxed at boil, or maintained under pressure at a temperature not lower than a boiling point.

As described herein, a time period during which the reaction solution is maintained at elevated temperatures means a time period until the residual initiator content reaches 0.05 weight % or less of a total weight of the reaction solution, on a solids content basis. Such a time period can be calculated by substituting characteristic values (frequency factor, activation energy) of the initiator used, a concentration of the initiator and a treatment temperature into the below-defined equations (1) and (2) for representing a reduction rate κ of the initiator concentration.

$$[I]/[I]_0 = e^{-\kappa t} \quad (1)$$

$$\kappa = A e^{-Ea/RT} \quad (2)$$

where, $[I]$ is a concentration of an initiator, $[I]_0$ is an initial (t=0) concentration of the initiator, t is a time period, A is a frequency factor, Ea is an activation energy, R is a gas constant, and T is a temperature (absolute temperature).

THE MEDICAL PRESSURE-SENSITIVE ADHESIVE

In accordance with a broad aspect of the present invention, a medical pressure-sensitive adhesive is provided which includes as its main component a copolymer obtainable by subjecting a monomer composition containing alkyl (meth)acrylate ester as its principal ingredient to a solution polymerization in the presence of an initiator that generates radicals, and which contains a residual initiator in the range not to exceed 0.05 weight % of a total weight of the adhesive, on a solids content basis. Since the residual initiator content, in this instance, is in the range not to exceed 0.05 weight % of a total weight of the adhesive, on a solids content basis, as described above, any undesirable change in adhesive properties of the medical pressure-sensitive adhesive with time is effectively prevented. As also stated above, it is more preferable that the content of the residual initiator is not higher than 0.01 weight %.

Illustrative of the method for reducing the residual initiator content to not higher than 0.05 weight % of a total weight, as stated above, is a method of copolymerizing the afore-described monomer composition under a closed condition at least in the latter stage of the polymerization reaction.

Also, in accordance with a particular aspect of the present invention, a medical pressure-sensitive adhesive prepared in such a manner as described above may be supported by a flexible backing to, as a whole, form an adhesive material in which the medical pressure-sensitive adhesive is incorporated as a constituent. Such adhesive materials may be used as adhesive bandages, medical dressing tapes and the like.

The above medical pressure-sensitive adhesive may further contain drugs. In such a case, the medical pressure-sensitive adhesive can be incorporated as a constituent in a medical adhesive material. Illustrative of the drugs which may be contained in the pressure-sensitive adhesive are, but not limited to, antiphlogistic analgesic, antiphlogistic, coronary vasodilator, tranquilizers, antihypertensive, antibiotic, anesthetic, antibacterial materials, antihistamines, sex hormones, brain circulatory improvers and antiulcers. The drug content varies depending upon its type, but is generally in the range of 0.1–30 weight % of the pressure-sensitive adhesive.

When necessary, an absorption accelerator, a solvent for the drug, a tackifier, a crosslinking agent, a filler, or an antioxidant may be suitably incorporated in the pressure-sensitive adhesive layer.

Again, in the case of the medical pressure-sensitive adhesive which further contains drugs, the medical pressure-sensitive adhesive is preferably supported by a flexible backing, as described above.

Illustrative materials applicable to the flexible backing for constituting the above-described adhesive materials include olefin derivatives such as polyethylene, polypropylene, polybutadiene, ethylene-vinyl acetate copolymer, ethylene-propylene copolymer, ethylene-alkyl (meth)acrylate copolymer, and polybutane; polystyrenes such as styrene-isoprene-styrene copolymer, styrene-butadiene-styrene copolymer, and hydrates thereof; vinylidene chloride derivatives such as polyvinylidene chloride and vinylidene chloride-styrene copolymer; vinyl chloride derivatives such as polyvinyl chloride, vinyl chloride-ethylene copolymer, and vinyl chloride-alkyl acrylate ester copolymer; silicone resins; polyesters such as polyethylene fluoride, polyethylene terephthalate, and polybutylene terephthalate, polyurethanes, and polyamides.

The flexible backing may also be of cotton or nonwoven fabrics laminated on films prepared from the above resins. In addition, the flexible backing may take any form such as films, sheets, or tapes.

While any particular range of flexibility is not specified for the flexible backing, it is preferred that the flexible backing be constructed to exhibit a sufficient flexibility to follow any motion of a human body, since it is applied to a human skin in use. The thickness of the flexible backing may vary depending upon the particular material used. In the case of a film-form backing, the thickness thereof may be not higher than 500 μm, preferably 40–200 μm.

For the purpose of enhancing adhesion to the pressure-sensitive adhesive layer, a surface of the film-form backing for supporting the pressure-sensitive adhesive layer may be optionally subjected to a treatment such as an undercoat processing, a corona discharge treatment, a chemical oxidization treatment, or an ozonization treatment.

The provision of the medical pressure-sensitive adhesive on the flexible backing results in the medical pressure-sensitive adhesive which takes the form as the medical adhesive material. Generally, a release paper is applied onto a surface of the pressure-sensitive adhesive layer of the adhesive material for shielding thereof from ambient atmosphere and for preventing the pressure-sensitive adhesive from adhering to other parts prior to its purposed use.

Where the medical pressure-sensitive adhesive of the present invention is incorporated as a constituent into the form of the adhesive material, it is preferable to place such a release paper on a surface of the pressure-sensitive adhesive. Those comprising polyethylene, polypropylene, or polyethylene terephthalate films can be employed as the release paper. The thickness of the release paper is generally not higher than 300 μm, preferably in the range of 10–200 μm.

In the preparation of the medical adhesive materials, conventional, general-purpose techniques can be suitably employed. Specifically, conventional techniques for coating pressure-sensitive adhesives, such as bar coating and gravure coating can be employed. The thickness of the pressure-sensitive adhesive layer is not particularly limited, but is generally in the range of 20–1000 μm. The thickness not exceeding 20 μm may be insufficient to incorporate a required amount of drugs in the pressure-sensitive adhesive layer and to provide a satisfactory pressure-sensitive adhesion. The thickness exceeding 1000 μm possibly causes poor diffusion of the drugs contained in the pressure-sensitive adhesive portion present in the vicinity of the backing so that the utilization of the drugs is reduced.

DESCRIPTION OF THE PREFERRED EXAMPLES

EXAMPLE 1

A closable, polymerization reactor having a pressure-resistant structure and equipped with a stirrer, temperature controller, nitrogen line, heating and cooling jackets was employed. The reactor was first purged with nitrogen gas to discharge air remaining in the reactor and maintained at vacuum pressure (about 60 mmHg). Supplied by suction into the reactor were 1000 g of ethyl acrylate, 800 g of octyl acrylate, 200 g of methyl methacrylate and 2000 g of ethyl acetate, each previously bubbled with nitrogen gas. While the mixture was stirred at a rate of 30 rpm and an interior of the reactor was maintained at 80° C., a 0.1 weight % solution of lauroyl peroxide in ethyl acetate was added thereto batchwise, i.e. 10 times at intervals of 2 hours to effect polymerization. An exothermic heat of the polymerization was controlled by reducing a jacket temperature (temperature of a heat transfer medium) so that the interior of the reactor was maintained at 80° C. The polymerization was continued for 24 hours. After cooling, ethyl acetate was introduced and mixed so that a polymer concentration was thinned to 30 weight %. A pressure-sensitive adhesive solution thus obtained was withdrawn from the reactor.

EXAMPLE 2

Polymerization was carried out in the same manner as in Example 1 except that the reaction temperature for polymerization was changed from 80° C. to 60° C.

EXAMPLE 3

A pressure-sensitive adhesive solution was obtained in accordance with the polymerization procedures of Example 1 with the modifications that lauroyl peroxide was replaced by benzoyl peroxide and the reaction temperature was changed from 80 °C. to 110° C.

EXAMPLE 4

A pressure-sensitive adhesive solution was obtained in accordance with the polymerization procedures of Example 1 with the following modifications: A mixture of 1600 g of 2-ethylhexyl methacrylate, 200 g of 2-ethylhexyl acrylate, 200 g of dodecyl methacrylate and 2000 g of ethyl acetate as a solvent was used as the monomer composition. The reaction temperature was changed to 60° C.

EXAMPLE 5

A pressure-sensitive adhesive solution was obtained in accordance with the polymerization procedures of Example 4 except that the reaction temperature was changed from 60° C. to 80° C.

EXAMPLE 6

A pressure-sensitive adhesive solution was obtained in accordance with the polymerization procedures of Example 4 with the modifications that lauroyl peroxide was replaced by benzoyl peroxide and the reaction temperature was changed to 110° C.

EXAMPLE 7

A pressure-sensitive adhesive solution was obtained in accordance with the polymerization procedures of Example 4 with the following modifications: A mixture of 800 g of 2-ethylhexyl methacrylate, 500 g of 2-ethylhexyl acrylate, 700 g of dodecyl methacrylate and 2000 g of ethyl acetate as a solvent was used as the monomer composition. The reaction temperature was changed to 80° C.

EXAMPLE 8

A pressure-sensitive adhesive solution was obtained in accordance with the polymerization procedures of Example 4 with the following modifications: A mixture of 1800 g of 2-ethylhexyl methacrylate, 200 g of 2-ethylhexyl acrylate and 2000 g of ethyl acetate as a solvent was used as the monomer composition. The reaction temperature was changed to 80° C.

COMPARATIVE EXAMPLE 1

A reflux condenser was mounted to one of the inlet lines of the polymerization reactor employed in Example 1 to open an upper portion thereof. The monomer composition and the solvent of Example 1 were introduced into the reactor. The interior atmosphere of the reactor was then substituted by nitrogen. The mixture was then heat refluxed while stirred at 30 rpm and charged with 30 ml/min of nitrogen. The jacket temperature was maintained at a temperature 3° C. higher than the interior temperature of the reactor. The 0.1 weight % solution of lauroyl peroxide in ethyl acetate was added in the same manner as in Example 1 to effect polymerization. Since the interior temperature of the reactor decreases as the polymerization proceeds, a control was applied to maintain the jacket temperature 3° C. above the interior temperature of the reactor. The polymerization was continued for 24 hours. After cooling, ethyl acetate was introduced and mixed so that a polymer concentration was thinned to 30 weight %. A pressure-sensitive adhesive solution was thus obtained.

COMPARATIVE EXAMPLE 2

A reflux condenser was mounted to one of the inlet lines of the polymerization reactor employed in Example 4 to open an upper portion thereof. The monomer composition of Example 1 was introduced into the reactor the interior atmosphere of which was then substituted by nitrogen. The mixture was then heat refluxed while stirred at 30 rpm and charged with 30 ml/min of nitrogen. The polymerization was performed initially at 90° C. and in about 10 hours at 80° C. while the 0.1 weight % solution of lauroyl peroxide in ethyl acetate, as a polymerization initiator, was added batchwise 10 times at time intervals of 2 hours. Since the interior temperature of the reactor decreases as the polymerization proceeds, controlling was applied to maintain the jacket temperature (temperature of heat transfer medium) at a temperature 3° C. above the interior temperature of the reactor. The polymerization was continued for 24 hours. After cooling, ethyl acetate was introduced and mixed so that a polymer concentration was thinned to 30 weight %. A pressure-sensitive adhesive solution was thus obtained.

COMPARATIVE EXAMPLE 3

A pressure-sensitive adhesive solution was prepared in the same manner as employed in Comparative Example 2 except that the monomer composition of Example 7 was used as a monomer composition.

COMPARATIVE EXAMPLE 4

A pressure-sensitive adhesive solution was prepared in the same manner as employed in Comparative Example 2 except that the monomer composition of Example 8 was used as a monomer composition.

A list of the formulations, solvents, polymerization initiators, and reaction temperatures employed respectively in Examples 1–8 and Comparative Examples 1–4, as described above, is provided in the following Tables 1 and 2. In Table 1 and 2, "EA" represents ethyl acrylate, "OA" represents octyl acrylate, "MMA" represents methyl methacrylate, "EHM" represents 2-ethylhexyl methacrylate, "EHA" represents 2-ethylhexyl acrylate, "DM" represents dodecyl methacrylate, and "EtAc" represents ethyl acetate. "LPO" and "BPO" as polymerization initiators represent lauroyl peroxide and benzoyl peroxide, respectively.

TABLE 1

| | ALKYL (METH)ACRYLATE ESTERS (g) | | | EtAc | | TEMP. |
|---|---|---|---|---|---|---|
| | EA | OA | MMA | (g) | INITIATOR | (°C.) |
| Example 1 | 1000 | 800 | 200 | 2000 | LPO | 80 |
| Example 2 | 1000 | 800 | 200 | 2000 | LPO | 60 |
| Example 3 | 1000 | 800 | 200 | 2000 | BPO | 110 |
| Comparative Example 1 | 1000 | 800 | 200 | 2000 | LPO | — |

TABLE 2

| | ALKYL (METH)ACRYLATE ESTERS (g) | | | EtAc | | TEMP. |
|---|---|---|---|---|---|---|
| | EHM | EHA | DM | (g) | INITIATOR | (°C.) |
| Example 4 | 1600 | 200 | 200 | 2000 | LPO | 60 |
| Example 5 | 1600 | 200 | 200 | 2000 | LPO | 80 |
| Example 6 | 1600 | 200 | 200 | 2000 | BPO | 110 |
| Example 7 | 800 | 500 | 700 | 2000 | LPO | 80 |
| Example 8 | 1800 | 200 | — | 2000 | LPO | 80 |
| Comparative Example 2 | 1600 | 200 | 200 | 2000 | LPO | — |
| Comparative Example 3 | 800 | 500 | 700 | 2000 | LPO | — |
| Comparative Example 4 | 1800 | 200 | — | 2000 | LPO | — |

EXAMPLES 9–18

A pressure-sensitive adhesive solution was obtained in the same manner as in Example 1 with the following modifications: Supplied into the reactor was a mixture of alkyl acrylate ester, vinyl pyrrolidone and ethyl acetate respectively in their predetermined amounts as listed in the following Table 3. The polymerization initiators and reaction temperatures as shown in the following Table 3 were utilized.

COMPARATIVE EXAMPLES 5–10

A pressure-sensitive adhesive solution was obtained in accordance with the polymerization procedures of Comparative Example 1 with the following modifications: A mixture of alkyl acrylate ester, vinyl pyrrolidone and ethyl acetate respectively in their predetermined amounts as listed in the following Table 3 was utilized.

In the following Table 3, the terms commensurate with those used in Tables 1 and 2 are intended to provide the same meanings. "VP" represents vinyl pyrrolidone. In each box on the VP column, the values given in top and bottom rows indicate a weight (g) and a proportion (mole %) of VP in the monomer composition, respectively.

TABLE 3

| | ALKYL (METH)ACRYLATE ESTERS (g) | | | VP (g) (mol %) | EtAc (g) | INITIATOR | TEMP. (°C.) |
|---|---|---|---|---|---|---|---|
| | EHA | OA | EA | | | | |
| Ex. 9 | 1500 | — | — | 500 / 35.6 | 2000 | LPO | 60 |
| Ex. 10 | 1500 | — | — | 500 / 35.6 | 2000 | LPO | 80 |
| Ex. 11 | 1500 | — | — | 500 / 35.6 | 2000 | BPO | 110 |
| Ex. 12 | 1900 | — | — | 100 / 8.0 | 2000 | LPO | 80 |
| Ex. 13 | 1100 | — | — | 900 / 57.6 | 2000 | LPO | 80 |
| Ex. 14 | — | 800 | 1000 | 200 / 11.2 | 2000 | LPO | 60 |
| Ex. 15 | — | 800 | 1000 | 200 / 11.2 | 2000 | LPO | 80 |
| Ex. 16 | — | 800 | 1000 | 200 / 11.2 | 2000 | BPO | 110 |
| Ex. 17 | — | 900 | 1000 | 100 / 5.7 | 2000 | LPO | 80 |
| Ex. 18 | — | 700 | 400 | 900 / 50.9 | 2000 | LPO | 80 |
| Comp. Ex. 5 | 1500 | — | — | 500 / 35.6 | 2000 | LPO | — |
| Comp. Ex. 6 | 1900 | — | — | 100 / 8.0 | 2000 | LPO | — |
| Comp. Ex. 7 | 1100 | — | — | 900 / 57.6 | 2000 | LPO | — |
| Comp. Ex. 8 | — | 800 | 1000 | 200 / 11.2 | 2000 | LPO | — |
| Comp. Ex. 9 | — | 900 | 1000 | 100 / 5.7 | 2000 | LPO | — |
| Comp. Ex. 10 | — | 700 | 400 | 900 / 50.9 | 2000 | LPO | — |

EXAMPLES 19–23

A pressure-sensitive adhesive solution was obtained in accordance with the polymerization procedures of Example 1 with the following modifications: Alkyl (meth)acrylate esters as shown in the following Table 4, polyfunctional monomers and ethyl acetate were utilized in their respective proportions as listed in the following Table 4. The polymerization initiators and the reaction temperatures were selected as shown in the following Table 4.

COMPARATIVE EXAMPLES 11–13

A pressure-sensitive adhesive solution was obtained in accordance with the polymerization procedures of Comparative Example 1 except that the monomer compositions contained alkyl (meth)acrylate esters and polyfunctional monomers in their respective proportions as listed in the following Table 4.

EXAMPLES 24–29

A pressure-sensitive adhesive solution was obtained in accordance with the polymerization procedures of Example 1 with the following modifications: Compositions containing alkyl (meth)acrylate esters shown in the following Table 5, vinyl pyrrolidone (VP), polyfunctional monomers and ethyl acetate were utilized in their respective proportions as given in the following Table 5. The polymerization initiators and the reaction temperatures were selected as listed in the following Table 5.

COMPARATIVE EXAMPLES 14 AND 15

A pressure-sensitive adhesive solution was obtained in accordance with the polymerization procedures of Comparative Example 1 except that the monomer compositions contained alkyl (meth)acrylate esters shown in the following Table 5, vinyl pyrrolidone and polyfunctional monomers in their respective proportions as listed in the following Table 5.

EXAMPLES 30–32

A pressure-sensitive adhesive solution was obtained in accordance with the polymerization procedures of Example 1 with the following modifications: Compositions containing alkyl (meth)acrylate esters shown in the following Table 6, polyfunctional monomers and ethyl acetate were utilized in their respective proportions as given in the following Table 6. The polymerization initiators and the reaction temperatures were selected as listed in the following Table 6.

COMPARATIVE EXAMPLE 16

A pressure-sensitive adhesive solution was obtained in accordance with the polymerization procedures of Comparative Example 1 except that the monomer compositions contained alkyl (meth)acrylate esters shown in the following Table 6 and polyfunctional monomers in their respective proportions as listed in the following Table 6.

In Tables 4, 5 and 6, if the terms used therein for representing respective monomers correspond to those used in Tables 1–3, they are intended to provide the same meanings. "BA" represents butyl acrylate, "BM" represents butyl methacrylate, "HDA" represents 1,6-hexanediol diacrylate ester, and "PGDM" represents polyethylene glycol dimethacrylate ester.

TABLE 4

| | ALKYL (METH)ACRYLATE ESTERS (mol) | | POLYFUNC. MONOMER (mol) | | ETHYL ACETATE (g) | INITIATOR (g) | TEMP. (°C.) |
|---|---|---|---|---|---|---|---|
| Ex. 19 | BA | — | HDA | | 2000 | LPO | 80 |
|  | 10 |  | 0.0008 |  |  |  |  |
| Ex. 20 | BA | — | HDA |  | 2000 | LPO | 60 |
|  | 10 |  | 0.0008 |  |  |  |  |
| Ex. 21 | BA | — | HDA |  | 2000 | BPO | 110 |
|  | 10 |  | 0.0008 |  |  |  |  |
| Ex. 22 | BA | BM | PGDM |  | 2000 | LPO | 80 |
|  | 6 | 4 | 0.0005 |  |  |  |  |
| Ex. 23 | BA | EA | HDA |  | 2000 | LPO | 80 |
|  | 8.5 | 1.5 | 0.004 |  |  |  |  |
| Comp. Ex. 11 | BA | — | HDA |  | 2000 | LPO | — |
|  | 10 |  | 0.0008 |  |  |  |  |
| Comp. Ex. 12 | BA | BM | PGDM |  | 2000 | LPO | — |
|  | 6 | 4 | 0.0005 |  |  |  |  |
| Comp. Ex. 13 | BA | EA | HDA |  | 2000 | LPO | — |
|  | 8.5 | 1.5 | 0.004 |  |  |  |  |

TABLE 5

| | ALKYL (METH)ACRYLATE ESTERS (g) | | | VP (g) (mol) | POLYFUNC. MONOMER | | EtAc (g) | INITIATOR | TEMP. (°C.) |
|---|---|---|---|---|---|---|---|---|---|
| | EHA (mol) | OA (mol) | EA (mol) | | TYPE | (g) (mol) | | | |
| Ex. 24 | 1500 8.14 | — | — | 500 4.50 | HDA | 0.227 0.001 | 2000 | LPO | 80 |
| Ex. 25 | 1500 8.14 | — | — | 500 4.50 | PGDM | 0.107 0.0005 | 2000 | LPO | 80 |
| Ex. 26 | 1500 8.14 | — | — | 500 4.50 | HDA | 0.045 0.0002 | 2000 | BPO | 110 |
| Ex. 27 | — | 800 4.34 | 1000 9.99 | 200 1.80 | HDA | 0.227 0.001 | 2000 | LPO | 80 |
| Ex. 28 | — | 800 4.34 | 1000 9.99 | 200 1.80 | PGDM | 0.107 0.0005 | 2000 | LPO | 80 |
| Ex. 29 | — | 800 4.34 | 1000 9.99 | 200 1.80 | HDA | 0.045 0.0002 | 2000 | BPO | 110 |
| Comp. Ex. 14 | 1500 8.14 | — | — | 500 4.50 | HDA | 0.227 0.001 | 2000 HDA | LPO | — |
| Comp. Ex. 15 | — | 800 4.34 | 1000 9.999 | 200 1.80 | HDA | 0.227 0.001 | 2000 | LPO | — |

TABLE 6

| | ALKYL (METH)ACRYLATE ESTERS (g) | | | POLYFUNC. MONOMER | | EtAc | INITIATOR | TEMP. (°C.) |
|---|---|---|---|---|---|---|---|---|
| | EHM (mol) | EHA (mol) | DM (mol) | TYPE | (g) (mol) | (g) | | |
| Ex. 30 | 1600 8.08 | 200 1.09 | 200 0.79 | HDA | 0.113 0.0005 | 2000 | LPO | 80 |
| Ex. 31 | 1400 7.07 | 300 1.63 | 300 1.18 | PGDM | 0.214 0.001 | 2000 | LPO | 80 |
| Ex. 32 | 1600 8.08 | 200 1.09 | 200 0.79 | HDA | 0.045 0.0002 | 2000 | BPO | 110 |
| Comp. Ex. 16 | 1600 8.08 | 200 1.09 | 200 0.79 | HDA | 0.113 0.0005 | 2000 | LPO | — |

EXAMPLES 33–39

A pressure-sensitive adhesive solution was obtained in accordance with the polymerization procedures of Example 1 with the following modifications: The monomer compositions were utilized which contained alkyl (meth)acrylate esters shown in the following Table 7, monomers having a polyfunctional group and ethyl acetate as the solvent in their respective proportions as given in the following Table 7. The polymerization initiators as shown in the following Table 7 were utilized as the polymerization initiator. The reaction temperature was set to values as listed in the following Table 7.

COMPARATIVE EXAMPLES 17–19

A pressure-sensitive adhesive solution was obtained in ccordance with the polymerization procedures of Comparative Example 1 with the following modifications: The alkyl (meth)acrylate esters shown in the following Table 7, monomers having a polyfunctional group and ethyl acetate were used in their respective proportions as given in the following Table 7. The polymerization initiators as shown in the following Table 7 were utilized, and the reaction temperature was set to temperatures as given in the following Table 7.

In the following Table 7, if the terms used therein for representing respective monomers and polymerization initiators correspond to those used in Tables 1–6, they are intended to provide the same meanings. "AAc" represents acrylic acid, "HEMA" represents hydroxylethyl methacrylate, "AAm" represents acrylamide, "GMA" represents glycidyl methacrylate, and "DAEA" represents dimethylaminoethyl acrylate.

TABLE 7

| | ALKYL (METH)ACRYLATE ESTERS (g) | | MONOMER HAVING REAC. FUNC. GP. (g) | | ETHYL ACETATE (g) | INITIATOR (g) | TEMP. (°C.) |
|---|---|---|---|---|---|---|---|
| Ex. 33 | EHA | 1900 | AAc | 100 | 2000 | LPO | 60 |
| Ex. 34 | EHA | 1900 | AAc | 100 | 2000 | LPO | 80 |
| Ex. 35 | EHA | 1900 | AAc | 100 | 2000 | BPO | 110 |
| Ex. 36 | BA | 1900 | HEMA | 100 | 2000 | LPO | 80 |
| Ex. 37 | OA | 1950 | AAm | 50 | 2000 | LPO | 80 |
| Ex. 38 | EHA | 1900 | GMA | 100 | 2000 | LPO | 80 |
| Ex. 39 | OA | 1900 | DAEA | 100 | 2000 | LPO | 80 |
| Comp. Ex. 17 | EHA | 1900 | AAc | 100 | 2000 | LPO | — |
| Comp. Ex. 18 | OA | 1900 | HEMA | 100 | 2000 | LPO | — |
| Comp. Ex. 19 | BA | 1950 | AAm | 50 | 2000 | LPO | — |

EXAMPLES 40–44

A pressure-sensitive adhesive solution was obtained in accordance with the polymerization procedures of Example 1 with the following modifications: The monomer compositions were utilized which contained alkyl (meth)acrylate esters shown in the following Table 8, acrylic acid, and ethyl acetate in their respective proportions as given in the following Table 8. Those shown in the following Table 7 were utilized as the polymerization initiator. The reaction temperature was set to values as listed in the following Table 8.

COMPARATIVE EXAMPLES 20–22

A pressure-sensitive adhesive solution was obtained in accordance with the polymerization procedures of Comparative Example 1 with the following modifications: The monomer compositions were utilized which contained alkyl (meth)acrylate esters shown in the following Table 8, acrylic acid, and ethyl acetate in their respective proportions as given in the following Table 8. Lauryl peroxide was used as the polymerization initiator.

In Table 8, if the terms used therein correspond to those used in Tables 1–7, they are intended to provide the same meanings.

TABLE 8

| | ALKYL (METH)ACRYLATE ESTERS (g) | | AAc (g) | EtAc (g) | INITIATOR (g) | TEMP. (°C.) |
|---|---|---|---|---|---|---|
| Ex. 40 | EHA | 1900 | 100 | 2000 | LPO | 60 |
| Ex. 41 | EHA | 1900 | 100 | 2000 | LPO | 80 |
| Ex. 42 | EHA | 1900 | 100 | 2000 | BPO | 110 |
| Ex. 43 | EHM | 1950 | 50 | 2000 | LPO | 80 |
| Ex. 44 | OA | 1800 | 200 | 2000 | LPO | 80 |
| Comp. Ex. 20 | EHA | 1900 | 100 | 2000 | LPO | — |
| Comp. Ex. 21 | EHM | 1950 | 50 | 2000 | LPO | — |
| Comp. Ex. 22 | OA | 1800 | 200 | 2000 | LPO | — |

The pressure-sensitive adhesive solutions obtained in the above Examples 1–44 and Comparative Examples 1–22 were withdrawn to thereafter observe whether or not gels deposited on the reactor walls. Furthermore, for the purpose of dissolving the gels deposited on the reactor walls, if they were present, ethyl acetate was introduced into the polymerization reactor, heated for 3 hours and refluxed for cleaning. After withdrawal of ethyl acetate, observation was made to see the remaining gel deposits.

The results showed that no deposition of gels on the reactor walls was noticed at a point when the withdrawal of ethyl acetate was completed, throughout Examples 1–44. In contrast, throughout Comparative Examples 1–22, the attachment of gels on the reactor walls was noticed at a point where the withdrawal of ethyl acetate was completed, and those attached gels were noticed in all those examples to remain even after cleaning was applied in the manner as described above.

EXAMPLES 45–50

A closable, polymerization reactor having a pressure-resistant structure and equipped with a stirrer, temperature controller, nitrogen line, heating and cooling jackets was employed. Monomers and a solvent(s) as specified in Table 9 were first introduced into an reactor maintained in its opened condition, stirred at 30 rpm while purged with nitrogen before a temperature thereof was elevated. The solution to be polymerized was then heat fluxed for about 30 minutes at a boiling point thereof to remove an excess of oxygen. The solution was thereafter cooled to an initial polymerization temperature. After an interior of the reactor was placed under a closed condition, benzoyl peroxide as a polymerization initiator was added to initiate polymerization. The addition of benzoyl peroxide was carried out batchwise in 4 stages such that 10% of its whole amount was added at an initial stage of the polymerization, 20% in an hour, 20% in 2 hours, and 50% in 3 hours from the initial stage. Table 10 shows (1) reaction temperatures, (2) pressures and (3) boiling points of solutions when the given reaction periods elapsed. The final conversions were measured by a gas chromatography. Those values in % are given in Table 10. The molecular weights of acrylic copolymers obtained are also given in Table 10.

COMPARATIVE EXAMPLES 23–28

Polymerization was carried out in the same manner as employed in Examples 45–50 except that the interior of the reactor was placed under an opened condition after cooled to initial polymerization temperatures as specified in Table 10. Table 11 shows (1) reaction temperatures, (2) pressures and (3) boiling points of solutions when the given reaction periods elapsed; final conversions; and molecular weights of acrylic copolymers obtained.

In Tables 9–11, "EA" represents ethyl acrylate, "BA" represents butyl acrylate, "2EHA" represents 2-ethylhexyl acrylate, "AAc" represents acrylic acid, and "EtAc" represents ethyl acetate, as acrylic copolymer constituent monomers.

TABLE 9

| | Example | | | Comparative Example | | |
|---|---|---|---|---|---|---|
| | 45–47 | 48, 49 | 50 | 23–25 | 26, 27 | 28 |
| MONOMERS | | | | | | |
| EA | 0 | 20 | 0 | 0 | 20 | 0 |
| BA | 80 | 50 | 50 | 80 | 50 | 50 |
| 2EHA | 17 | 25 | 48 | 17 | 25 | 48 |
| AAc | 3 | 5 | 2 | 3 | 5 | 2 |
| SOLVENTS | | | | | | |
| EtAc | 100 | 80 | 60 | 100 | 80 | 60 |
| TOLUENE | 0 | 20 | 40 | 0 | 20 | 40 |
| INITIATOR | 0.05 | 0.20 | 0.5 | 0.05 | 0.20 | 0.5 |

*IN UNIT OF PARTS BY WEIGHT

TABLE 10

IN THE LAPSE OF HOURS
(1) REAC. TEMP. (2) PRESS. (3) B.P. OF SOLN.

| Ex. No. | ELAPSED TIME | 0 | 2 | 4 | 6 | 8 (HR.) | CONV. (%) | MOL. WT. |
|---|---|---|---|---|---|---|---|---|
| 45 | (1) | 93 | 85 | 90 | 88 | 85 (°C.) | 99.3 | 0.2 mill. |
| | (2) | 1 | → | 2 | → | (atm) | | |
| | (3) | 93 | 85 | 83 | 81 | 80 (°C.) | | |
| 46 | (1) | 98 | 95 | 88 | 86 | 85 (°C.) | 99.7 | 0.2 mill. |
| | (2) | 2 | → | → | → | (atm) | | |
| | (3) | 93 | 85 | 83 | 81 | 80 (°C.) | | |
| 47 | (1) | 80 | 80 | 90 | 90 | 90 (°C.) | 99.5 | 0.2 mill. |
| | (2) | 0.3 → | 0.5 → | 2 → | 2.5 → | 3 (atm) | | |
| | (3) | 93 | 85 | 83 | 81 | 80 (°C.) | | |
| 48 | (1) | 80 | 80 | 80 | 95 | 93 (°C.) | 99.7 | 0.25 mill. |
| | (2) | 0.2 → | 0.5 → | 0.8 → | 2 → | 2 (atm) | | |
| | (3) | 98 | 92 | 86 | 83 | 82 (°C.) | | |

TABLE 10-continued

| | | IN THE LAPSE OF HOURS (1) REAC. TEMP. (2) PRESS. (3) B.P. OF SOLN. | | | | | | |
|---|---|---|---|---|---|---|---|---|
| Ex. No. | ELAPSED TIME | 0 | 2 | 4 | 6 | 8 (HR.) | CONV. (%) | MOL. WT. |
| 49 | (1) | 105 | 100 | 97 | 95 | 93 (°C.) | 99.9 | 0.25 mill. |
|    | (2) | 2 | → | → | → | (atm) | | |
|    | (3) | 98 | 92 | 86 | 83 | 82 (°C.) | | |
| 50 | (1) | 100 | 100 | 100 | 100 | 100 (°C.) | 99.8 | 0.1 mill. |
|    | (2) | 0.5 → | 0.8 → | 1 → | 1.5 → | 2 (atm) | | |
|    | (3) | 108 | 104 | 100 | 95 | 90 (°C.) | | |

TABLE 11

| | | IN THE LAPSE OF HOURS (1) REAC. TEMP. (2) PRESS. (3) B.P. OF SOLN. | | | | | | |
|---|---|---|---|---|---|---|---|---|
| Comp. Ex. No. | ELAPSED TIME | 0 | 2 | 4 | 6 | 8 (HR.) | CONV. (%) | MOL. WT. |
| 23 | (1) | 93 | 85 | 83 | 81 | 80 (°C.) | 97.0 | 0.2 mill. |
|    | (2) | 1 | → | → | → | (atm) | | |
|    | (3) | 93 | 85 | 83 | 81 | 80 (°C.) | | |
| 24 | (1) | 80 | 80 | 80 | 80 | 80 (°C.) | 93.2 | 0.2 mill. |
|    | (2) | 1 | → | → | → | (atm) | | |
|    | (3) | 93 | 85 | 83 | 81 | 80 (°C.) | | |
| 25 | (1) | 80 | 80 | 80 | 79 | 78 (°C.) | 95.5 | 0.2 mill. |
|    | (2) | 0.3 → | 0.5 → | 1 | → | (atm) | | |
|    | (3) | 93 | 85 | 83 | 81 | 80 (°C.) | | |
| 26 | (1) | 80 | 80 | 80 | 80 | 80 (°C.) | 93.7 | 0.25 mill. |
|    | (2) | 0.2 → | 0.5 → | 0.8 → | 0.9 → | 1 (atm) | | |
|    | (3) | 98 | 92 | 86 | 83 | 82 (°C.) | | |
| 27 | (1) | 98 | 92 | 86 | 83 | 82 (°C.) | 98.3 | 0.25 mill. |
|    | (2) | 1 | → | → | → | (atm) | | |
|    | (3) | 98 | 92 | 86 | 83 | 82 (°C.) | | |
| 28 | (1) | 108 | 104 | 100 | 95 | 90 (°C.) | 98.7 | 0.1 mill. |
|    | (2) | 1 | → | → | → | (atm) | | |
|    | (3) | 108 | 104 | 100 | 95 | 90 (°C.) | | |

EXAMPLES 51–59

A five-necked flask equipped with a stirrer, thermometer, reflux condenser, nitrogen line and dropping funnel was employed. Into the flask is charged predetermined amounts of monomers and ethyl acetate as shown in Table 12. An interior of the flask was then substituted by nitrogen. The solution was stirred at 30 rpm while charged with nitrogen before its temperature was elevated. Thereafter, the solution was refluxed for about 30 minutes at a boiling point thereof to discharge an excess of oxygen, followed by cooling to polymerization temperatures as given in Table 13.

1.0 g of lauroyl peroxide was dissolved into ethyl acetate until a whole amount thereof reaches 30 ml to prepare an initiator solution. Polymerization was carried out by dropping the initiator solution in such patterns as shown in the following Table 13 into the monomer solutions maintained at their respective polymerization temperatures. After the polymerization was completed, ethyl acetate was introduced into a system for mixing therewith so that a solids concentration reached 30 weight %. The pressure-sensitive adhesive solutions were thus prepared.

COMPARATIVE EXAMPLES 29–34

Polymerization was carried out utilizing the equipments used in Examples 51–59 and in the same manner as in Examples 51–59. However, the predetermined amounts of monomers and ethyl acetate as given in the following Table 12 were introduced, and such polymerization conditions as indicated in Table 13 were utilized. After the polymerization was completed, ethyl acetate was introduced into a system for mixing therewith so that a solids concentration reached 30 weight %, as also performed in Examples 51–59. The pressure-sensitive adhesive solutions were thus prepared.

EXAMPLES 60–68

A closed, polymerization reactor having a pressure-resistant structure and equipped with a stirrer, temperature controller, nitrogen line, reflux condenser, heating and cooling jackets was employed.

The nitrogen gas was purged into the reactor to discharge air remaining in the reactor, and subsequently removed by a vacuum pump to maintain the interior of the reactor under a degree of vacuum at about 60 mmHg. The predetermined amounts of monomers and ethyl acetate, previously bubbled with nitrogen gas, were supplied by suction into the reactor in their respective proportions as given in the following Table 14.

The monomer solution was then stirred at 30 rpm while the interior of the reactor was maintained at polymerization temperatures specified in the following Table 15.

The reactor was maintained under a closed condition in Examples 60, 61, 63, 64, 66 and 67, and a top of the reflux condenser was remained open in Examples 62, 65 and 68. In Examples 51–68, the following procedures were taken into practice.

An initiator solution was prepared in the same manner as employed in Example 51. Polymerization was carried out by dropping the initiator solution in such patterns as shown in the following Table 15 into the monomer solutions maintained at their respective polymerization temperatures. However, in Examples 62, 65 and 68, the polymerization reactor was brought into a closed condition after the final introduction of the initiator solution was made, before the polymerization was performed.

Again, in Examples 60–68, after the polymerization was completed, ethyl acetate was introduced into a system for mixing therewith so that a solids content therein reached 30 weight %, as performed in Examples 51–59. The pressure-sensitive adhesive solutions were thus prepared.

COMPARATIVE EXAMPLES 35–40

Utilizing the equipments as employed in Examples 60–68, polymerization was carried out in the nitrogen stream under the conditions as specified in the following Table 15, wherein the monomers and ethyl acetate were supplied in the predetermined amounts as given in the following Table 14 and the top of the reflux condenser was maintained opened from the beginning till the end.

After the polymerization was completed, ethyl acetate was introduced and mixed so that a solids concentration therein reached 30 weight %. The pressure-sensitive adhesive solutions were thus prepared.

The terms as used in Table 12 and Table 13 for indicating monomers have the following meanings:

EHA . . . 2-ethylhexyl acrylate, EA . . . ethyl acrylate, OA . . . octyl acrylate, VP . . . N-vinyl pyrrolidone, EHMA . . . 2-ethylhexyl methacrylate, DM . . . dodecyl methacrylate.

TABLE 12

| | MONOMERS (g) | | | | | | ETHYL ACETATE |
|---|---|---|---|---|---|---|---|
| | EHA | EA | OA | VP | EHMA | DM | (g) |
| Example 51 | 75 | | | 25 | | | 100 |
| Example 52 | 75 | | | 25 | | | 150 |
| Example 53 | 75 | | | 25 | | | 100 |
| Example 54 | | 50 | 40 | 10 | | | 100 |
| Example 55 | | 50 | 40 | 10 | | | 150 |
| Example 56 | | 50 | 40 | 10 | | | 150 |
| Example 57 | 10 | | | | 78 | 12 | 50 |
| Example 58 | 10 | | | | 78 | 12 | 75 |
| Example 59 | 10 | | | | 78 | 12 | 50 |
| Comparative Example 29 | 75 | | | 25 | | | 100 |
| Comparative Example 30 | 75 | | | 25 | | | 100 |
| Comparative Example 31 | | 50 | 40 | 10 | | | 150 |
| Comparative Example 32 | | 50 | 40 | 10 | | | 150 |
| Comparative Example 33 | 10 | | | | 78 | 12 | 50 |
| Comparative Example 34 | 10 | | | | 78 | 12 | 50 |

TABLE 13

| | POL. TEMP. | AMT. OF INITIATOR ADDED AT THE LAPST OF HOURS DURING POLYMERIZATION (ml) | | | | | | | | POL. TIME |
|---|---|---|---|---|---|---|---|---|---|---|
| | (°C.) | 0 H | 2 H | 4 H | 6 H | 8 H | 10 H | 15 H | 20 H | (h) |
| Ex. 51 | 75*) | 0.3 | 0.3 | 0.3 | 0.6 | 1.5 | 3.0 | 9.0 | 15.0 | 25 |
| Ex. 52 | 70*) | 0.3 | 0.3 | 0.3 | 0.6 | 1.5 | 3.0 | 9.0 | 15.0 | 26 |
| Ex. 53 | 60*) | 0.5 | 0.5 | 1.0 | 1.0 | 2.0 | 5.0 | 5.0 | 15.0 | 30 |
| Ex. 54 | 75 | 0.3 | 0.3 | 0.3 | 0.6 | 1.5 | 3.0 | 9.0 | 15.0 | 30 |
| Ex. 55 | 70*) | 0.3 | 0.3 | 0.3 | 0.6 | 1.5 | 3.0 | 9.0 | 15.0 | 30 |
| Ex. 56 | 60*) | 0.5 | 0.5 | 1.0 | 1.0 | 2.0 | 5.0 | 5.0 | 15.0 | 26 |
| Ex. 57 | 75*) | 0.3 | 0.3 | 0.3 | 0.6 | 1.5 | 3.0 | 9.0 | 15.0 | 25 |
| Ex. 58 | 70*) | 0.3 | 0.3 | 0.3 | 0.6 | 1.5 | 3.0 | 9.0 | 15.0 | 26 |
| Ex. 59 | 60*) | 0.5 | 0.5 | 1.0 | 1.0 | 2.0 | 5.0 | 5.0 | 15.0 | 30 |
| Comp. Ex. 29 | 75 | 0.3 | 0.3 | 0.3 | 0.6 | 1.5 | 3.0 | 9.0 | 15.0 | 23 |
| Comp. Ex. 30 | 60 | 0.5 | 0.5 | 1.0 | 1.0 | 2.0 | 5.0 | 5.0 | 15.0 | 25 |
| Comp. Ex. 31 | 75 | 0.3 | 0.3 | 0.3 | 0.6 | 1.5 | 3.0 | 9.0 | 15.0 | 25 |
| Comp. Ex. 32 | 60*) | 0.5 | 0.5 | 1.0 | 1.0 | 2.0 | 5.0 | 5.0 | 15.0 | 23 |
| Comp. Ex. 33 | 75 | 0.3 | 0.3 | 0.3 | 0.6 | 1.5 | 3.0 | 9.0 | 15.0 | 23 |
| Comp. Ex. 34 | 60 | 0.5 | 0.5 | 1.0 | 1.0 | 2.0 | 5.0 | 5.0 | 15.0 | 25 |

TABLE 14

| | MONOMERS (g) | | | | | | ETHYL ACETATE |
|---|---|---|---|---|---|---|---|
| | EHA | EA | OA | VP | EHMA | DM | (g) |
| Example 60 | 75 | | | 25 | | | 100 |
| Example 61 | 75 | | | 25 | | | 150 |
| Example 62 | 75 | | | 25 | | | 100 |
| Example 63 | | 50 | 40 | 10 | | | 100 |
| Example 64 | | 50 | 40 | 10 | | | 150 |
| Example 65 | | 50 | 40 | 10 | | | 150 |
| Example 66 | 10 | | | | 78 | 12 | 50 |
| Example 67 | 10 | | | | 78 | 12 | 75 |
| Example 68 | 10 | | | | 78 | 12 | 50 |
| Comparative | 75 | | | 25 | | | 100 |

TABLE 14-continued

|  | MONOMERS (g) | | | | | ETHYL ACETATE |
|---|---|---|---|---|---|---|
|  | EHA | EA | OA | VP | EHMA | DM | (g) |
| Example 35 |  |  |  |  |  |  |  |
| Comparative Example 36 | 75 |  |  | 25 |  |  | 100 |
| Comparative Example 37 |  | 50 | 40 | 10 |  |  | 150 |
| Comparative Example 38 |  | 50 | 40 | 10 |  |  | 150 |
| Comparative Example 39 | 10 |  |  |  | 78 | 12 | 50 |
| Comparative Example 40 | 10 |  |  |  | 78 | 12 | 50 |

TABLE 15

| | POL. TEMP. | AMT. OF INITIATOR ADDED AT THE LAPST OF HOURS DURING POLYMERIZATION (ml) | | | | | | | | POL. TIME |
|---|---|---|---|---|---|---|---|---|---|---|
| | (°C.) | 0 H | 2 H | 4 H | 6 H | 8 H | 10 H | 15 H | 20 H | (h) |
| Ex. 60 | 70/100 | 0.3 | 0.3 | 0.3 | 0.6 | 1.5 | 3.0 | 9.0 | 15.0 | 21.0 |
| Ex. 61 | 70/90 | 0.3 | 0.3 | 0.3 | 0.6 | 1.5 | 3.0 | 9.0 | 15.0 | 21.5 |
| Ex. 62 | 60/110 | 0.5 | 0.5 | 1.0 | 1.0 | 2.0 | 5.0 | 5.0 | 15.0 | 21.0 |
| Ex. 63 | 75/85 | 0.3 | 0.3 | 0.3 | 0.6 | 1.5 | 3.0 | 9.0 | 15.0 | 22.0 |
| Ex. 64 | 70/90 | 0.3 | 0.3 | 0.3 | 0.6 | 1.5 | 3.0 | 9.0 | 15.0 | 21.5 |
| Ex. 65 | 60/100 | 0.5 | 0.5 | 1.0 | 1.0 | 2.0 | 5.0 | 5.0 | 15.0 | 20.5 |
| Ex. 66 | 70/100 | 0.3 | 0.3 | 0.3 | 0.6 | 1.5 | 3.0 | 9.0 | 15.0 | 21.0 |
| Ex. 67 | 70/90 | 0.3 | 0.3 | 0.3 | 0.6 | 1.5 | 3.0 | 9.0 | 15.0 | 21.5 |
| Ex. 68 | 60/110 | 0.5 | 0.5 | 1.0 | 1.0 | 2.0 | 5.0 | 5.0 | 15.0 | 21.0 |
| Comp. Ex. 35 | 70 | 0.3 | 0.3 | 0.3 | 0.6 | 1.5 | 3.0 | 9.0 | 15.0 | 28.0 |
| Comp. Ex. 36 | 60 | 0.5 | 0.5 | 1.0 | 1.0 | 2.0 | 5.0 | 5.0 | 15.0 | 30.0 |
| Comp. Ex. 37 | 70/77 | 0.3 | 0.3 | 0.3 | 0.6 | 1.5 | 3.0 | 9.0 | 15.0 | 24.0 |
| Comp. Ex. 38 | 60/77 | 0.5 | 0.5 | 1.0 | 1.0 | 2.0 | 5.0 | 5.0 | 15.0 | 25.0 |
| Comp. Ex. 39 | 70 | 0.3 | 0.3 | 0.3 | 0.6 | 1.5 | 3.0 | 9.0 | 15.0 | 28.0 |
| Comp. Ex. 40 | 60 | 0.5 | 0.5 | 1.0 | 1.0 | 2.0 | 5.0 | 5.0 | 15.0 | 30.0 |

In Table 13, the polymerization temperatures to which an asterisk * is given mean that they were elevated after the lapse of 20 hours from the initiation of polymerization for refluxing at boil (liquid temperature=77° C.).

In Table 15, the polymerization temperature is given, throughout Examples 60–68, as (temperature maintained within 20 hours from the initiation of polymerization)/(temperature maintained after the lapse of 20 hours from the initiation of polymerization). For example, 70/100, as given in Example 60, means that the temperature was maintained at 70° C. within 20 hours from the initiation of polymerization and that the temperature was maintained at 100° C. after the lapse of 20 hours from the initiation of polymerization.

Also in Comparative Examples 37 and 38, the solution was refluxed at boil (liquid temperature=77° C.) after the lapse of 20 hours from the initiation of polymerization.

EVALUATION OF EXAMPLES AND COMPARATIVE EXAMPLES

The concentration of the polymerization initiator remaining in the resulting pressure-sensitive adhesives was determined by one of methods for analyzing active oxygens in peroxides, i.e. an iodine titration method (titration with a $\frac{1}{10}$N sodium thiosulfate solution), using an iodine compound (potassium iodide). The determined concentrations in weight % relative to a total solids content in the pressure-sensitive adhesive are given in Table 16 and Table 17.

(2) HOLDING POWER EVALUATION OF THE PRESSURE SENSITIVE ADHESIVE AFTER INCORPORATED INTO A MEDICAL ADHESIVE MATERIAL

For the pressure-sensitive adhesive solutions obtained in Examples 51–55 and 60–64, and Comparative Examples 29–32 and 35–38, each pressure-sensitive adhesive solution was knife coated onto a silicone surface of a polyethylene terephthalate film and thereafter dried to form a coating having a thickness of 50 μm. The coating was applied to a substrate comprising a laminated film of polyethylene terephthalate and ethylene-vinyl acetate copolymer to form a laminate.

For the pressure-sensitive adhesive solutions obtained in Examples 56 and 65, mixed with each pressure-sensitive solution was isosorbide nitrate in its concentration of 10 weight % relative to a total solids content. The mixture was knife coated onto a silicone surface of a polyethylene terephthalate film and thereafter dried to form a coating having a thickness of 50 μm. The coating was applied to a substrate comprising a laminated film of polyethylene terephthalate and ethylene-vinyl acetate copolymer to form a laminate.

For the pressure-sensitive adhesive solutions obtained in Examples 57–59 and 60–68, and Comparative Examples 33, 34, 39 and 40, mixed with each pressure-sensitive solution was nitroglycerin in its concentration of 10 weight % relative to a total solids content. The mixture was knife coated onto a silicone surface of a polyethylene terephthalate film and thereafter dried to form a coating having a thickness of 50 μm. The coating was applied to a substrate comprising a laminated film of polyethylene terephthalate and ethylene-vinyl acetate copolymer to form a laminate.

In either cases, the drying of the coated pressure-sensitive adhesives was effected at 60° C. for 30 minutes to prepare the medical adhesive materials. Also, a portion of each medical adhesive material obtained was cut apart to provide a pressure-sensitive tape which was then sealed within an aluminum package for placement in a constant temperature bath maintained at 60° C. for 2 weeks (acceleration test).

In evaluating the change of adhesive properties with time, the holding power was measured in the following procedures for each medical adhesive material left 3 days after the pressure-sensitive adhesive was coated, and for each medical adhesive material subjected to the above acceleration test.

Holding power measurement . . . A strip of 25 mm wide and 150 mm long was prepared. The strip was adhered to a stainless steel plate so as to be in contact therewith in an area of 25×25 mm. The unadhered portion of the strip was folded toward inside, that is, a pressure-sensitive adhesive layer was folded onto itself. A pressure was applied for bonding thereof by one reciprocal movement of a 2 kg roller over the test piece at a speed of 300 mm/min. A sample comprising the above test piece bonded to a stainless steel plate was held in a constant temperature bath maintained at 40° C. for 20 minutes or longer. One end of the test piece was then secured by a fastener so that the test piece was suspended vertically. A 1 kg weight was attached to an end portion of the unadhered, folded part, and a time period (holding time period) until the weight dropped was measured. The results are given in the following Table 16 and Table 17.

TABLE 16

| | RESIDUAL INITIATOR | HOLDING TIME (MIN.) | |
|---|---|---|---|
| | (wt. %) | AFTER COATING | AFTER ACC. TEST |
| Example 51 | 0.037 | 52 | 55 |
| Example 52 | 0.021 | 39 | 40 |
| Example 53 | 0.000 | 65 | 65 |
| Example 54 | 0.009 | 224 | 226 |
| Example 55 | 0.000 | 175 | 176 |
| Example 56 | 0.029 | 38 | 39 |
| Example 57 | 0.045 | 25 | 28 |
| Example 58 | 0.028 | 18 | 19 |
| Example 59 | 0.000 | 29 | 28 |
| Comparative Example 29 | 0.154 | 58 | 114 |
| Comparative Example 30 | 0.364 | 72 | 298 |
| Comparative Example 31 | 0.067 | 236 | 354 |
| Comparative Example 32 | 0.143 | 294 | 579 |
| Comparative Example 33 | 0.208 | 27 | 48 |
| Comparative Example 34 | 0.459 | 35 | 109 |

TABLE 17

| | RESIDUAL INITIATOR | HOLDING TIME (MIN.) | |
|---|---|---|---|
| | (wt. %) | AFTER COATING | AFTER ACC. TEST |
| Example 60 | 0.001 | 58 | 60 |
| Example 61 | 0.016 | 41 | 47 |
| Example 62 | 0.000 | 74 | 72 |
| Example 63 | 0.038 | 241 | 259 |
| Example 64 | 0.022 | 182 | 189 |
| Example 65 | 0.037 | 32 | 34 |
| Example 66 | 0.002 | 23 | 24 |
| Example 67 | 0.023 | 19 | 21 |
| Example 68 | 0.000 | 27 | 28 |
| Comparative Example 35 | 0.101 | 52 | 107 |
| Comparative Example 36 | 0.348 | 78 | 263 |
| Comparative Example 37 | 0.073 | 227 | 341 |

TABLE 17-continued

| | RESIDUAL INITIATOR | HOLDING TIME (MIN.) | |
|---|---|---|---|
| | (wt. %) | AFTER COATING | AFTER ACC. TEST |
| Comparative Example 38 | 0.052 | 212 | 324 |
| Comparative Example 39 | 0.135 | 29 | 41 |
| Comparative Example 40 | 0.447 | 38 | 112 |

For the pressure-sensitive adhesives of Examples 51–68, the residual initiator contents thereof are all within 0.05 weight %, as apparent from Table 16 and Table 17. It is accordingly understood that the above holding time period shows little change between after coating and after the acceleration test.

In contrast, the residual initiator contents are high, i.e. not lower than 0.05 weight % in Comparative Examples 29–40. In probable association with this, the strips subjected to the acceleration test are found to show a marked increase in holding power relative to those after coating. It is accordingly considered that the use of the medical adhesive materials of Comparative Examples 29–40 for application to a skin surface possibly causes significant discomfort during use since their holding powers are markedly increased as stated above.

In Comparative Example 32 wherein the temperature was increased in the latter stage of the polymerization to reflux at boil, the reduction of the residual initiator content was not sufficient, probably due to the shortened treatment period, so that the holding power after subjected to the acceleration test was significantly increased. Similarly, in Comparative Examples 37 and 38 wherein refluxing at the highest reaction temperature, i.e. at boil was effected in the latter stage of the polymerization using conventional open-system facilities, the residual initiator contents were only reduced to 0.073 weight % and 0.052 weight %, respectively, as apparent from Table 17. For this reason, the rather increased holding powers resulted after the acceleration test relative to those after coating, as apparent from Table 17.

EFFECTS OF THE INVENTION

As hereinbefore described, in accordance with the process of the present invention for preparing a solvent-type pressure-sensitive adhesive, the monomer composition containing alkyl (meth)acrylate ester as its main component is subjected to solution polymerization under a closed condition at least in the latter stage of the polymerization, which enables prevention of the solvent from being refluxed during the polymerization reaction to result in the largely reduced deposition of gels on the reactor walls. This significantly improves workability in the step of cleaning the reactor after the preparation of the pressure-sensitive adhesive was completed, and enables the increased productivity of the solvent-type acrylic adhesive.

Also, since the solvent-type acrylic adhesives thus obtained retain no gels, they can be suitably employed as medical pressure-sensitive adhesives. In addition, the formulations suitable for use in a medical adhesive material can be prepared utilizing the solvent-type acrylic adhesives.

Also, in the present invention, since the solution polymerization is carried out under a closed condition at least in the latter stage of the polymerization reaction, the polymerization reaction can be effected at temperatures not lower than a boiling point of the solvent at normal pressures. This enables an enhanced conversion to result in an increased productivity as well as a reduced residual monomers content whereby odor problems associated with the residual monomers can be solved.

In the process of the present invention for preparing a solvent-type acrylic adhesive, the solution polymerization is carried out under a closed condition at reaction temperatures in the range of 50°–120° C. This eliminates the necessity of a prolonged polymerization to result in an increased productivity, and also facilitates controlling the polymerization reaction.

Also, in the process of the present invention for preparing a solvent-type acrylic adhesive, when the solution polymerization is carried out such that a residual initiator content in the pressure-sensitive adhesive is not higher than 0.05 weight % of a total weight, based on a solids content basis, the low, residual initiator content is effective in preventing the pressure-sensitive adhesive from changing with time in adhesive properties, particularly in holding power. Accordingly, in the case that the medical pressure-sensitive adhesive is constructed using such a solvent-type acrylic adhesive, the discomfort given to users can be reduced since the adhesive properties of the pressure-sensitive adhesive layer hardly change with time. That is, any stress or irritation to skin can be reduced. Also, since its pressure-sensitive adhesion is hard to change with time, the separation or partial lifting of the medical adhesive materials from skin during use thereof can be prevented.

Also, the solvent-type acrylic pressure-sensitive adhesives having the residual initiator content within 0.05 weight % of a total weight thereof, on a solids content basis, can be obtained reliably and efficiently in a short period by subjecting the monomer composition containing alkyl (meth)acrylate ester as its main ingredient to solution polymerization in the presence of the initiator which generates radicals and under a closed condition at least in the latter stage of the polymerization reaction.

Furthermore, in the process of the present invention for preparing a solvent-type acrylic pressure-sensitive adhesive, alkyl (meth)acrylate ester and vinyl monomers copolymerizable with alkyl (meth)acrylate ester are utilized as the monomer composition containing alkyl (meth)acrylate ester as its main ingredient when preparing the solvent-type acrylic pressure-sensitive adhesive including as its main component the acrylic copolymer having a number average molecular weight of 10,000–500,000. In this instance, if the solution polymerization is carried out under a closed condition at least in the latter stage of the polymerization reaction, the reaction temperatures can be set to not lower than the boiling point of the monomer solution under normal pressures, so that the conversion can be increased and odors associated with the presence of residual monomers can be reduced.

We claim:

1. A medical pressure-sensitive adhesive which has as its main component a copolymer prepared by subjecting a monomer composition containing alkyl (meth) acrylate ester as its main ingredient to solution polymerization under vacuum in the presence of an initiator which generates radicals, said medical pressure-sensitive adhesive having a residual initiator content not higher than 0.05 weight % of a total weight, on a solid content basis.

2. The medical pressure-sensitive adhesive as set forth in claim 1 wherein said copolymer is polymerized under a closed condition at least in the latter stage of the polymerization so that the residual initiator content is not higher than 0.05 weight % of a total weight on a solids content basis.

3. The medical pressure-sensitive adhesive as set forth in claim 1 or 2 characterized in that said medical pressure-sensitive adhesive is supported on a flexible backing to take a form of an adhesive material.

4. The medical pressure-sensitive adhesive as set forth in claim 1 or 2 characterized by further containing drugs.

5. The medical pressure-sensitive adhesive as set forth in claim 4 characterized in that said medical pressure-sensitive adhesive is supported on a flexible backing to take a form of an adhesive material.

6. A process for preparing an acrylic pressure-sensitive adhesive wherein a monomer composition containing alkyl (meth)acrylate ester as its main component is subjected to solution polymerization under a closed condition at least in a latter stage of the polymerization reaction in the presence of a radical initiator such that the residual initiator content in the pressure-sensitive adhesive is not higher than 0.05 weight % of the total weight on a solids content basis.

7. The process for preparing an acrylic pressure-sensitive adhesive as set forth in claim 1, wherein said monomer composition is subjected to solution polymerization at reaction temperatures not lower than the boiling point of the solution to be polymerized.

8. The process for preparing an acrylic pressure-sensitive adhesive as set forth in claim 1, wherein polymerization is effected at reaction temperatures in the range of 50°–120° C. when said solution polymerization under the closed condition is carried out.

9. The process for preparing an acrylic pressure-sensitive adhesive as set forth in any one of claims 1–3, wherein said monomer composition includes alkyl (meth)acrylate ester carrying an alkyl group having 2–12 carbon atoms and vinyl monomers copolymerizable with the alkyl (meth)acrylate ester.

10. The process for preparing an acrylic pressure-sensitive adhesive as set forth in any one of claims 1–3, wherein said monomer composition is alkyl (meth)acrylate ester carrying an alkyl group having 6 or more carbon atoms which contains 40–90 weight % of 2-ethylhexyl methacrylate.

11. The process for preparing an acrylic pressure-sensitive adhesive as set forth in any of claims 1–3, wherein said monomer composition includes 40–99 mole % of alkyl (meth)acrylate ester and 1–60 mole % of vinyl pyrrolidone.

12. The process for preparing an acrylic pressure-sensitive adhesive as set forth in claim 4, wherein said monomer composition is a composition which includes alkyl (meth)acrylate ester and a polyfunctional monomer having 2 or more polymerizable double bonds per molecule and contains 0.01–0.1 moles of the polyfunctional monomer per 100 moles of said alkyl (meth)acrylate ester.

13. The process for preparing an acrylic pressure-sensitive adhesive as set forth in any one of claims 1–3, wherein said monomer composition contains alkyl (meth) acrylate ester and 1–10 weight % of a monomer having at least one functional group selected from the group consisting of carboxyl, hydroxyl, amide, epoxy and amino groups.

14. The process for preparing an acrylic pressure-sensitive adhesive as set forth in claim 13, wherein said monomer having at least one functional group selected from the group consisting of carboxyl, hydroxyl, amide, epoxy and amino groups is (meth)acrylic acid.

15. The medical pressure-sensitive adhesive as set forth in claim 2, wherein a conversion is higher than 95% in said latter stage of the polymerization.

16. The medical pressure-sensitive adhesive as set forth in claim 1, wherein the polymerization is performed under vacuum pressure of from 10 to 200 mmHg.

17. The process for preparing an acrylic pressure-sensitive adhesive as set forth in claim 6, wherein a conversion is higher than 95% in said latter stage of the polymerization.

18. The process for preparing an acrylic pressure-sensitive adhesive as set forth in claim 6, wherein the polymerization is performed under vacuum pressure of from 10 to 200 mmHg.

19. The process for preparing an acrylic pressure-sensitive adhesive as set forth in claim 6, wherein the polymerization is effected at reaction temperatures in the range of 60° to 100° C.

* * * * *